(12) United States Patent
Aljundi

(10) Patent No.: US 10,125,061 B2
(45) Date of Patent: Nov. 13, 2018

(54) METHOD OF OXIDATIVE DEHYDROGENATION OF HYDROCARBON COMPOUNDS

(71) Applicant: KING FAHD UNIVERSITY OF PETROLEUM AND MINERALS, Dhahran (SA)

(72) Inventor: Isam Aljundi, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 0 days.

(21) Appl. No.: 15/487,155

(22) Filed: Apr. 13, 2017

(65) Prior Publication Data

US 2018/0297914 A1    Oct. 18, 2018

(51) Int. Cl.

| | | |
|---|---|---|
| C07C 5/48 | (2006.01) | |
| C07C 5/42 | (2006.01) | |
| B01J 37/00 | (2006.01) | |
| B01J 23/843 | (2006.01) | |
| B01J 37/04 | (2006.01) | |
| B01J 37/02 | (2006.01) | |
| B01J 37/08 | (2006.01) | |
| B01J 35/02 | (2006.01) | |

(52) U.S. Cl.
CPC ............ *C07C 5/48* (2013.01); *B01J 23/8437* (2013.01); *B01J 35/023* (2013.01); *B01J 37/0009* (2013.01); *B01J 37/009* (2013.01); *B01J 37/0027* (2013.01); *B01J 37/0221* (2013.01); *B01J 37/0236* (2013.01); *B01J 37/04* (2013.01); *B01J 37/08* (2013.01); *C07C 2521/18* (2013.01); *C07C 2523/843* (2013.01)

(58) Field of Classification Search
CPC ............... C07C 5/48; C07C 5/42; C07C 5/00
See application file for complete search history.

(56) References Cited

U.S. PATENT DOCUMENTS

| | | | | |
|---|---|---|---|---|
| 1,930,716 A | * | 10/1933 | Jaeger | ............... B01D 53/8668 502/177 |
| 3,745,194 A | * | 7/1973 | Bertus et al. | ........ B01J 23/8437 585/624 |
| 3,865,750 A | * | 2/1975 | Rase | ...................... B01J 23/74 208/112 |
| 7,754,647 B2 | | 7/2010 | Schubert et al. | |
| 8,809,226 B2 | | 8/2014 | Song et al. | |
| 8,846,996 B2 | * | 9/2014 | Kustov | ................. B01J 23/002 241/24.12 |
| 8,927,455 B2 | | 1/2015 | Cho et al. | |
| 2003/0097034 A1 | | 5/2003 | Liu | |

FOREIGN PATENT DOCUMENTS

KR    10-2010-0028702    3/2010

OTHER PUBLICATIONS

Jermy, B.R., et al., "Influence of Calcination on Performance of Bi—Ni—O/Gamma-Alumina Catalyst for N-Butane Oxidative Dehydrogenation to Butadiene", Catalysis Science & Technology, vol. 5, pp. 4622-4635, (2015).

An, W., et al., "Catalytic Activity of Bimetallic Nickel Alloys for Solid-Oxide Fuel Cell Anode Reactions from Density-Functional Theory", Journal of Power Sources, vol. 196, pp. 4724-4728, (2011).

* cited by examiner

*Primary Examiner* — Youngsul Jeong
(74) *Attorney, Agent, or Firm* — Oblon, McClelland, Maier & Neustadt, L.L.P.

(57) ABSTRACT

A method of oxidative dehydrogenating a butane-containing hydrocarbon stream by contacting the same with a bimetallic catalyst in the presence of an oxidant, wherein the bimetallic catalyst comprises nickel and bismuth on a titanium carbide catalyst support. Various embodiments of the method of oxidative dehydrogenating the butane-containing hydrocarbon stream and the bimetallic catalyst are also provided.

15 Claims, No Drawings

METHOD OF OXIDATIVE DEHYDROGENATION OF HYDROCARBON COMPOUNDS

BACKGROUND OF THE INVENTION

Technical Field

The present invention relates to a method for oxidative dehydrogenation of a butane-containing hydrocarbon stream by contacting the same with a bimetallic catalyst that includes bismuth and nickel on a titanium carbide catalyst support.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Catalytic dehydrogenation of alkanes is a common step in the production of olefins, such as, for example, butene, propylene, or ethylene. Among catalytic dehydrogenation processes, direct dehydrogenation processes suffer from equilibrium limitations and thus high temperature conditions may be needed to obtain desirable alkene yields. Such high temperature processes may cause formation of cracked hydrocarbon products (via thermal cracking reactions) and oxygenated compounds (via oxidation or partial oxidation reactions). On the other hand, oxidative dehydrogenation processes are exothermic and generally suffer from low selectivity and inferior olefins quality. For such oxidative dehydrogenation processes, selecting an appropriate catalyst composition that can provide a higher selectivity, and subsequently a higher yield of olefin compounds is important.

Several research studies have been conducted to find an appropriate catalyst composition for oxidative dehydrogenation of alkanes, particularly oxidative dehydrogenation of butane. For example, the U.S. Pat. No. 8,927,455 describes a technique for preparing magnesia-zirconia catalyst supported by a synthesized carrier for oxidative dehydrogenation of n-butane to n-butene (i.e. 1-butene, cis-2-butene, trans-2-butene) and 1,3-butadiene. However, the maximum selectivity with respect to desired dehydrogenated products (i.e. i.e. 1-butene, cis-2-butene, trans-2-butene, and 1,3-butadiene) was found to be about 54.4% at a temperature of about 500° C. using a VMgO/MgO—$ZrO_2$ catalyst having 9.0 wt % vanadium. In addition, the U.S. Pat. No. 8,809,226 relates to a method for preparation of carrier-supported magnesium ortho-vanadate catalyst used for oxidative dehydrogenation of n-butane to butene and butadiene. The disclosed catalyst of this reference provided a maximum selectivity of about 61.4% with respect to the desired dehydrogenated products (i.e. butene and butadiene) at a relatively low butane conversion (i.e. about 2.5%) and a very low product yield (i.e. about 1.6%).

In view of the forgoing, one objective of the present invention is to provide a method for oxidative dehydrogenation of a butane-containing hydrocarbon stream by contacting the same with a bimetallic catalyst that includes bismuth and nickel on a titanium carbide catalyst support. The method can produce desired dehydrogenated products (i.e. 1-butene, cis-2-butene, trans-2-butene, and 1,3-butadiene) with a selectivity of at least 80% and a butane conversion of 10% to 20% at a reaction temperature of 350 to 500° C. Another objective of the present invention relates to a method of producing the bimetallic catalyst.

According to a first aspect, the present disclosure relates to a method of dehydrogenating a butane-containing hydrocarbon stream, involving contacting the butane-containing hydrocarbon stream with a bimetallic catalyst in the presence of oxygen to form a product stream comprising a butene compound, wherein the bimetallic catalyst comprises nickel and bismuth on a titanium carbide catalyst support.

In one embodiment, the butene compound is one or more of 1-butene, cis-2-butene, trans-2-butene, 1,3-butadiene, and isobutylene.

In one embodiment, a weight percent of nickel in the bimetallic catalyst is within the range of 15 wt % to 25 wt %, relative to the total weight of the bimetallic catalyst.

In one embodiment, a weight percent of bismuth in the bimetallic catalyst is within the range of 25 wt % to 35 wt %, relative to the total weight of the bimetallic catalyst.

In one embodiment, the butane-containing hydrocarbon stream is contacted with the bimetallic catalyst at a temperature of 300 to 500° C.

In one embodiment, a volume fraction of butane in the butane-containing hydrocarbon stream is at least 0.9.

In one embodiment, a molar ratio of oxygen to butane is in the range of 1:1 to 1:4.

In one embodiment, the bimetallic catalyst has an average particle size in the range of 0.1 to 2 mm.

In one embodiment, the bimetallic catalyst further comprises nickel oxide and bismuth oxide.

In one embodiment, the product stream further comprises non-butene compounds, wherein a molar ratio of the butene compound to the non-butene compounds is at least 0.8.

In one embodiment, a conversion of butane is in the range of 5 to 30 mol %, wherein a yield of the butene compound is in the range of 5% to 20% based on the conversion of butane.

In one embodiment, the method of dehydrogenating further involves treating the bimetallic catalyst with an inert gas having a temperature in the range of 300 to 600° C. prior to the contacting.

In one embodiment, the method of dehydrogenating further involves mixing the butane-containing hydrocarbon stream with oxygen and an inert gas to form a gaseous mixture prior to the contacting, wherein a volume fraction of the butane-containing hydrocarbon stream in the gaseous mixture is within the range of 0.01 to 0.1, preferably about 0.04.

According to a second aspect, the present disclosure relates to a method of producing a bimetallic catalyst comprising nickel and bismuth on a titanium carbide catalyst support, the method involves i) dissolving a nickel precursor and a bismuth precursor in water to form a Ni—Bi solution, ii) mixing and stirring titanium carbide with the Ni—Bi solution to form a suspension comprising the bimetallic catalyst, wherein nickel and bismuth are deposited on a surface of the titanium carbide.

In one embodiment, the method of producing the bimetallic catalyst further involves i) drying the suspension to form a powder of the bimetallic catalyst, ii) pressing the powder to form pellets of the bimetallic catalyst, iii) crushing and sieving the pellets to form bimetallic catalyst granules with an average particle size in the range of 0.1 to 2 mm.

In one embodiment, the method of producing the bimetallic catalyst further involves i) calcining the bimetallic catalyst granules at a temperature in the range of 300 to 400°

C. for no more than 2 hours, ii) calcining the bimetallic catalyst granules at a temperature in the range of 550 to 650° C. for no more than 3 hours, wherein said granules are calcined in an inert atmosphere.

In one embodiment, the nickel precursor is nickel nitrate hexahydrate, and the bismuth precursor is bismuth nitrate pentahydrate.

In one embodiment, a weight ratio of bismuth to nickel in the suspension is in the range of 1:1 to 2:1.

In one embodiment, a concentration of nickel in the Ni—Bi solution is in the range of 5 to 7 g/L, and a concentration of bismuth in the Ni—Bi solution is in the range of 7 to 9 g/L.

According to a third aspect, the present disclosure relates to a bimetallic catalyst comprising nickel and bismuth on a titanium carbide catalyst support, wherein the bimetallic catalyst has an average particle size in the range of 0.1 to 2 mm.

The foregoing paragraphs have been provided by way of general introduction, and are not intended to limit the scope of the following claims. The described embodiments, together with further advantages, will be best understood by reference to the following detailed description taken in conjunction with the accompanying drawings.

DETAILED DESCRIPTION OF THE EMBODIMENTS

According to a first aspect, the present disclosure relates to a bimetallic catalyst comprising nickel and bismuth on a titanium carbide catalyst support.

In a preferred embodiment, nickel as used in the bimetallic catalyst refers to elemental nickel, although in some embodiments, nickel as used in the bimetallic catalyst is present in the form of a nickel oxide, a nickel salt, or mixtures thereof. Additionally, in a preferred embodiment, bismuth as used in the bimetallic catalyst refers to elemental bismuth, although in some embodiments, bismuth as used in the bimetallic catalyst is present in the form of a bismuth oxide, a bismuth salt, or mixtures thereof. Furthermore, in some embodiments, the bimetallic catalyst includes elemental nickel and one or more of a nickel oxide and a nickel salt; also the bimetallic catalyst includes elemental bismuth and one or more of a bismuth oxide and a bismuth salt. In an alternative embodiment, nickel and bismuth as used in the bimetallic catalyst are present in a form of a bimetallic alloy of NiBi and/or $Ni_xBi_y$, wherein x and y are integers in the range of 1 to 10, preferably 1 to 5, preferably 1 to 3.

In one embodiment, a weight percent of nickel (present as elemental nickel, a nickel oxide, and/or a nickel salt) in the bimetallic catalyst is within the range of 15 wt % to 25 wt %, preferably 16 wt % to 24 wt %, preferably 17 wt % to 23 wt %, preferably 18 wt % to 22 wt %, preferably 19 wt % to 21 wt %, preferably about 20 wt %, relative to the total weight of the bimetallic catalyst. In another embodiment, a weight percent of bismuth (present as elemental bismuth, a bismuth oxide, and/or a bismuth salt) in the bimetallic catalyst is within the range of 25 wt % to 35 wt %, preferably 26 wt % to 34 wt %, preferably 27 wt % to 33 wt %, preferably 28 wt % to 32 wt %, preferably 29 wt % to 3 wt %, preferably about 30 wt %, relative to the total weight of the bimetallic catalyst. In an alternative embodiment, a weight ratio of bismuth to nickel in the bimetallic catalyst is in the range of 1:1 to 3:1, preferably 1.1:1 to 2:1, preferably 1.2:1 to 1.8:1, preferably 1.3:1 to 1.5:1, preferably about 1.4:1. In some embodiments, nickel and bismuth as used in the bimetallic catalyst are nanoparticles with an average particle size in the range of 5 to 50 nm, preferably 8 to 30 nm, preferably 10 to 15 nm that are deposited on a surface of the titanium carbide catalyst support.

The term "bimetallic catalyst" as used herein refers to a catalyst that includes nickel and bismuth as major metallic elements (i.e. having a weight percent of at least 15 wt %, preferably at least 18 wt %, preferably at least 20 wt %, relative to the total weight of the bimetallic catalyst), and thus provide a major contribution to catalyze the oxidative dehydrogenation reactions. However, the titanium present in the titanium carbide catalyst support may also be a catalytically active element (i.e. the titanium may catalyze the oxidative dehydrogenation reactions), and thus the titanium carbide catalyst support may catalyze the oxidative dehydrogenation reactions.

The term "bimetallic" is not meant to be limiting to two metallic elements, and thus more than two metallic elements may also be present in a composition of the bimetallic catalyst. However, metallic elements other than nickel and bismuth may also be present as minor elements (i.e. having a weight percent of up to 10 wt %, preferably up to 8 wt %, preferably up to 5 wt %, and down to 0.01 wt %, preferably down to 0.05 wt %, preferably down to 0.1 wt %, relative to the total weight of the bimetallic catalyst). Accordingly, in one embodiment, the bimetallic catalyst includes a third element selected from titanium (Ti) (i.e. present only as elemental titanium or titanium oxide), tantalum (Ta), niobium (Nb), cobalt (Co), hafnium (Hf), tungsten (W), yttrium (Y), zinc (Zn), zirconium (Zr), aluminum (Al), and/or a compound containing one or more of such element(s) for example oxides or salts of such elements, or mixtures thereof. Preferably, a weight percent of the third element may be less than 10 wt %, preferably less than 8 wt %, preferably less than 5 wt %, and down to 0.01 wt %, preferably down to 0.05 wt %, preferably down to 0.1 wt % relative to the total weight of the bimetallic catalyst. Alternatively, the third element may be an alkali metal, an alkaline earth metal, an oxide thereof, a salt thereof, or a mixture of such elements or compounds. For example, in one embodiment, the third element is selected from the group consisting of Ca, K, Mg, Sr, Ba, Li, and Na, most preferably Ca, K and Mg, and in either case, oxides thereof and salts thereof, or mixtures of such elements or compounds. In one embodiment, the third element is a basic metal oxide to adjust an acidity of the bimetallic catalyst. An oxide of an element is an oxide thereof where the respective element is in an oxidation state other than the fully-reduced state, and includes oxides having an oxidation states corresponding to known stable valence numbers, as well as to oxides in partially reduced oxidation states. In addition, a salt of an element can be any stable salt thereof, including, for example, nitrates, carbonates, and acetates. Preferably, other metals that are not listed above may not be present in the bimetallic catalyst.

In a preferred embodiment, the titanium carbide catalyst support is a porous support with a pore size ranging from 2 nm to 100 nm, preferably 5 nm to 80 nm, preferably 10 nm to 60 nm, preferably 15 nm to 50 nm, preferably 20 nm to 40 nm. Additionally, the titanium carbide catalyst support may have a surface area ranging from 5 $m^2/g$ to 300 $m^2/g$, preferably 10 $m^2/g$ to 250 $m^2/g$, preferably 15 $m^2/g$ to 200 $m^2/g$, preferably 20 $m^2/g$ to 150 $m^2/g$, preferably 25 $m^2/g$ to 100 $m^2/g$. In view of this embodiment, nickel, bismuth, and/or the third element (if present) may be present on a surface of the titanium carbide catalyst support, or inside the pores.

In another embodiment, the bimetallic catalyst includes a second catalyst support selected from the group consisting of silica, alumina, zeolite, activated carbon, titania, zirconia, and magnesia. Preferably, the second catalyst support is at least one selected from titania, zirconia, alumina, and silica. Preferably, the second catalyst support is used in the composition of the bimetallic catalyst to adjust a porosity and/or a surface area of the bimetallic catalyst. In view of that, a weight percent of the second catalyst support relative to the weight of the titanium carbide catalyst support is no more than 20%, preferably no more than 15%, preferably no more than 10%. In the embodiments where the second catalyst support contains a catalytically active element (e.g., $Al_2O_3$ that contains aluminum), the second catalyst support may catalyze the oxidative dehydrogenation reactions. In some other embodiments, the second catalyst support is inert, and does not participate in the oxidative dehydrogenation reactions.

In one embodiment, the bimetallic catalyst may be mixed with binders and/or diluents, which are known to those of skilled in the art to reduce a concentration and an acidity of the bimetallic catalyst. Diluents may be added to the catalyst in the range of 0 to 30 vol %, preferably 5 to 25 vol %, preferably 10 to 20 vol %, relative to the total volume of a catalyst bed that houses the catalyst and the diluents. The diluents may improve the heat removal or heat transfer of the bimetallic catalyst to help avoid hot spots or to modify hot spots. Additionally, binders may provide mechanical strength to the catalyst and may be added to the bimetallic catalyst in the range of 0 to 30 vol %, preferably 5 to 25 vol %, preferably 10 to 20 vol %, relative to the total volume of the catalyst/binder. Preferable binders include silica sol, silica, alumina, diamataceous earth, hydrated zirconia, silica aluminas, alumina phosphates, naturally occurring materials and cement and combinations thereof. Preferable diluents include, for example, quartz chips, sands, clay and/or cement.

Preferably, the bimetallic catalyst may be pressed to form in disc-shape pellets having a diameter in the range of 0.1-2 min, preferably 0.2-1.5 mm, more preferably about 1 mm. The bimetallic catalyst may also be pressed to form a powder, granules, pellets, extrudates, or a shaped catalyst. Accordingly, the bimetallic catalyst may have a cylindrical (solid or hollow cylindrical), a spherical, a rectilinear, a star-shape, a ring-shape, a conical, a pyramidal, a rectangular, or a cubical geometry with an average particle size in the range of 0.1-2 mm, preferably 0.2-1.5 mm, more preferably about 1 mm. Shaping of the bimetallic catalyst may be carried out by compaction (for example tableting or extrusion) of a solid catalyst mixture with or without a prior kneading step, if necessary with addition of conventional auxiliaries (e.g., graphite or stearic acid or its salts as lubricants). In some embodiments, the solid catalyst mixture may be shaped either before or after calcining the catalyst, for example, by grinding the solid catalyst mixture before or after calcination.

According to a second aspect, the present disclosure relates to a method of dehydrogenating a butane-containing hydrocarbon stream.

"Dehydrogenation" as used herein refers to is a chemical reaction that involves removal of hydrogen from an organic molecule. In addition, "oxidative dehydrogenation" refers to a chemical reaction that involves the removal of hydrogen from an organic molecule in the presence of an oxidant such as molecular oxygen.

Accordingly, the butane-containing hydrocarbon stream is contacted with the bimetallic catalyst in the presence of an oxidant, wherein at least a portion of butane present in the butane-containing hydrocarbon stream is oxidatively dehydrogenated. As a result, a product stream that includes one or more butene compounds and one or more non-butene compounds may form via an oxidative dehydrogenation reaction as following:

$$C_4H_{10} + \tfrac{1}{2}O_2 \rightarrow C_4H_8 + H_2O$$

In one embodiment, the butane-containing hydrocarbon stream includes butane and one or more hydrocarbon compounds selected from the group consisting of alkanes, olefins, diolefins, aromatics, and oxymoron. The term "alkane" as used herein refers to saturated straight-chain, saturated branched, or saturated cyclic hydrocarbons having a carbon number in the range of 1 to 12, preferably 2 to 6, such as methane, ethane, propane, pentane, hexane, etc. The term "olefin" as used here refers to unsaturated straight-chain, unsaturated branched, or unsaturated cyclic hydrocarbons having a carbon number in the range of 1 to 12 preferably 2 to 5, such as ethylene, propylene, 1-butene, cis- and trans-2-butene, pentene, hexane, etc. Exemplary diolefin compounds that may be present in the butane-containing hydrocarbon stream include, but are not limited to propadiene, butadiene, pentadiene, etc. Additionally, exemplary oxymoron compounds that may be present in the butane-containing hydrocarbon stream include, but are not limited water, tert-butanol, methyl tert-butyl ether, methanol, ethanol, acetic acid, acetaldehyde, etc. In one embodiment, a volume fraction of butane in the butane-containing hydrocarbon stream is at least 0.9, preferably at least 0.92, preferably at least 0.95, preferably at least 0.98, preferably at least 0.99. In some embodiments, the butane-containing hydrocarbon stream is in liquid state, and a mass fraction of butane in the butane-containing hydrocarbon stream is at least 0.6, preferably at least 0.7, preferably at least 0.8, preferably at least 0.9. Preferably, a volume fraction of non-butane compounds present in the butane-containing hydrocarbon stream is no more than 0.1, preferably no more than 0.08, preferably no more than 0.05, preferably no more than 0.02. Exemplary non-butane compounds that may be present in the butane-containing hydrocarbon stream include, but are not limited to, methane, ethane, propane, pentane, hexane, ethylene, propylene, pentene, hexane, propadiene, butadiene, pentadiene, tert-butanol, methyl tert-butyl ether, methanol, ethanol, acetic acid, acetaldehyde, water, etc.

The butane-containing hydrocarbon stream may be an effluent of a debutanizer, a fluid catalytic cracker, a steam cracker, a separation column, or a combination thereof.

In an alternative embodiment, at least a portion of the alkane present in the butane-containing hydrocarbon stream is oxidatively dehydrogenated in the presence of the bimetallic catalyst and the oxidant, via an oxidative dehydrogenation reaction as following:

$$C_nH_{2n+2} + \tfrac{1}{2}O_2 \rightarrow C_nH_{2n} + H_2O$$

wherein hydrogen atoms combine with an oxygen from the oxidant to form respective alkenes and water as a reaction by-product.

In one embodiment, the butane-containing hydrocarbon stream is in a gaseous state when contacted with the bimetallic catalyst. In another embodiment, the butane-containing hydrocarbon stream is in a double phase liquid/gaseous state, wherein liquid reactants present in the butane-containing hydrocarbon stream may be vaporized by methods and devices known in the art prior to be contacted with the bimetallic catalyst. Alternatively, the butane-containing hydrocarbon stream may be in a liquid state.

The oxidant is preferably a gaseous oxidant, but may also include a liquid oxidant or a solid-state oxidant. The gaseous oxidant is preferably molecular oxygen, and may be present as an oxygen stream or as an oxygen-containing stream. The oxygen-containing stream may be air, or an oxygen stream that has been diluted with one or more inert gases such as nitrogen, argon, helium, etc. Other gaseous oxidants, such as $N_2O$, NO, or $NO_2$ may also be used for the oxidative dehydrogenating the butane-containing hydrocarbon stream. In embodiments wherein a solid-state oxidant is used, the oxidant may be periodically regenerated. In a preferred embodiment, the oxidant is an oxygen-containing stream which is mixed with the butane-containing hydrocarbon stream such that a molar ratio of oxygen to butane is in the range of 1:1 to 1:4, preferably 1:1 to 1:3, preferably 1:1 to 1:2.

In one embodiment, the bimetallic catalyst is housed in a catalyst bed of a reactor, and the butane-containing hydrocarbon stream and the oxidant are delivered to the reactor either together as a mixed gas through a common feed line, or separately but simultaneously via different feed lines. The reactor may preferably be a fixed-bed reactor, although other reactors such as a batch reactor or a fluidized bed reactor may also be employed.

In one embodiment, the butane-containing hydrocarbon stream is mixed with an inert gas to form a gaseous mixture prior to be contacted with the bimetallic catalyst. Accordingly, a volume fraction of the butane-containing hydrocarbon stream in the gaseous mixture is within the range of 0.01 to 0.1, preferably 0.02 to 0.08, preferably 0.03 to 0.05, preferably about 0.04. Preferably, the inert gas may be at least one gas selected from nitrogen, argon, and carbon dioxide.

In one embodiment, the butane-containing hydrocarbon stream, the oxidant, and the bimetallic catalyst may be contacted by passing a mixture of the butane-containing hydrocarbon stream and the oxidant through a fixed-bed reactor packed with the bimetallic catalyst, or by passing said mixture over an exposed surface of the bimetallic catalyst. The contact time (or residence tune) may vary, however, a preferably contact time may range from about 0.1 seconds to about 10 seconds, preferably from about 0.5 seconds to about 8 seconds, preferably from about 1 seconds to about 5 seconds. In another embodiment, the butane-containing hydrocarbon stream and the oxidant are in gaseous state, wherein a gas space velocity may range from about 100/hr to about 10,000/hr, preferably from about 300/hr to about 6,000/hr, and more preferably from about 300/hr to about 2,000/hr. In one embodiment, the inert gas is used to adjust the gas space velocity. In another embodiment, the butane-containing hydrocarbon stream and the oxidant are contacted with the bimetallic catalyst at a temperature that ranges from about 300° C. to about 600° C., more preferably from about 320° C. to about 550° C., even more preferably from about 350° C. to about 520° C., still more preferably from about 375° C. to about 500° C., and yet more preferably from about 390° C. to about 475° C., and most preferably from about 400° C. to about 470° C. In another embodiment, the butane-containing hydrocarbon stream and the oxidant are contacted with the bimetallic catalyst at a pressure that ranges from atmospheric pressure (i.e. 1 atm) to about 20 bar, preferably from about 1.5 bar to about 10 bar, preferably from about 2 bar to about 8 bar, preferably from about 2.5 bar to about 5 bar.

The product stream includes one or more butene compounds, one or more of non-butene compounds, and water. Preferably, said butene compound is one or more of 1-butene, cis-2-butene, trans-2-butene, 1,3-butadiene, and isobutylene that are produced from n-butane or i-butane. In one embodiment, the non-butene compounds include ethylene (e.g. produced from ethane) and propylene (e.g. produced from propane). In one embodiment, halide-substituted alkanes (preferably having a carbon number of 2 to 5) are oxidatively dehydrogenated using the bimetallic catalyst to form vinyl halides. For example, ethyl chloride may be oxidatively dehydrogenated using the bimetallic catalyst and methods described herein to form vinyl chloride. In addition, the product stream may further include unreacted alkanes, an unreacted oxidant, as well as side-products (e.g., $CO_2$). The butene compound (i.e. 1-butene, cis-2-butene, trans-2-butene, isobutylene, and/or 1,3-butadiene) may be separated from the product stream by methods known in the art. Preferably, for example, the butene compound may be recovered from the product stream by cryogenic separation, by pressure-swing adsorption (e.g., on zeolites), by selective absorption, etc.

In an alternative embodiment, the product stream may be used, without further separation or with partial separation (e.g., with a removal of $CO_2$ and/or $H_2O$) as a feed stream to a downstream reactor, where the alkene product can be reacted further.

In some embodiments, the butene compound (i.e. one or more of 1-butene, cis-2-butene, trans-2-butene, 1,3-butadiene, and isobutylene that are produced via an oxidative dehydrogenation of n-butane and/or i-butane) may be further reacted to form methacrylic acid, butanol, butanediol, butadiene, methylethylketone (MEK), methylvinylketone (MVK), furan, or crotonaldehyde.

In another embodiment, the isobutene or n-butene can optionally be purified, and then further reacted according to one or more of the following schemes. For example, isobutene may be oxidized to form methacrylic acid according to methods known in the art using a catalyst comprising an element or compound having activity for oxidizing isobutene to methacrylic acid (e.g. catalysts that include polyoxometallate (POM), preferably PVMo- or PVW-containing POM). Butanol may be prepared by hydrating n-butene to form butanol. Alternatively, n-butene may be oxidatively dehydrogenated to form butadiene according to methods known in the art) using a catalyst comprising an element or compound having activity for oxidatively dehydrogenating n-butene to butadiene (e.g. catalysts that include elements or compounds selected from the group consisting of Ni, Ti, Ta, Nb, Hf, W, Y, Zn, Zr, Al, oxides thereof, and salts thereof, or mixtures of such elements or compounds). Butanediol may also be prepared by forming butadiene, as described above, and then hydrating butadiene to form butanediol. Moreover, n-butene may be oxidatively dehydrogenated to form butadiene, and butadiene can be oxidized to form methylethylketone (MEK) according to the methods known in the art using a catalyst comprising an element or compound having activity for oxidation of butadiene to MEK (e.g. catalysts that include Bi/Mo, Mo/V/W, VPO or a polyoxometallate). Alternatively, n-butene may be oxidatively dehydrogenated to form butadiene (as described above), and butadiene can be oxidized to form methylvinylketone (MVK) according to the methods known in the art using a catalyst comprising an element or compound having activity for oxidation of butadiene to MVK (e.g. catalysts that include Bi/Mo, Mo/V/W, VPO or a polyoxometallate). In one embodiment, furan is prepared by oxidizing n-butene.

Crotonaldehyde can also be prepared by forming butadiene, as described above, and oxidizing butadiene to form crotonaldehyde.

In one embodiment, the product stream includes ethylene as a non-butene compound. In some embodiments, ethylene produced via oxidative dehydrogenation of ethane using the bimetallic catalyst may be further reacted to form polyethylene, styrene, ethanol, acetaldehyde, acetic acid, vinyl chloride, ethylene oxide, ethylene glycol, ethylene carbonate, ethyl acetate, and vinyl acetate. For example, ethylene may be polymerized to form polyethylene according to methods known in the art using a catalyst having activity for polymerizing ethylene to polyethylene. Exemplary polymerization approaches include free-radical polymerization and polymerization over Ziegler-Natta (i.e., metal alkyl) catalysts. Ethylene may also be reacted with benzene in the presence of acid catalysts such as aluminum chloride or zeolites to form ethylbenzene, which may further be catalytically dehydrogenated (using the bimetallic catalyst of the invention or known dehydrogenation catalysts) to form styrene. Styrene may also be formed directly from a reaction of ethylene and benzene. Moreover, ethylene may be hydrated to form ethanol according to methods known in the art using a catalyst comprising an element or compound having activity for hydrating ethylene to ethanol (e.g. catalysts that include oxides of B, Ga, Al, Sn, Sb or Zn, or mixtures of such oxides), along with a water stream that is preferably co-fed to a reaction zone during the hydration reaction. Acetaldehyde may also be formed from ethylene according to methods known in the art either directly or through an ethanol intermediate. Accordingly, ethylene can be oxidized to acetaldehyde using a catalyst comprising an element or a compound having activity for oxidizing ethylene to acetaldehyde (e.g. catalysts that include oxides of Pd, Cu, V or Co, or mixtures of such oxides). Alternatively, ethylene may be hydrated to form ethanol and ethanol is then oxidized to form acetaldehyde in the presence of a catalyst having activity for oxidizing ethanol to acetaldehyde (e.g. catalysts that include metals and/or metal oxides of Cu, Co, Ag, Re, Ru, Pt, Bi, Ce, Sb, In, Pd, Rh, Ir, V, Cr or Mn, or mixtures of such oxides). Furthermore, ethylene may be oxidized to form acetic acid according to methods known in the art using a catalyst comprising an element or compound having activity for oxidizing ethylene to acetic acid (e.g. catalysts that include a noble metal or an oxide thereof, preferably Pd or Pt or oxides thereof), along with a water stream that is preferably co-fed to a reaction zone during the ethylene oxidation reaction. Besides, ethylene may be chlorinated or oxychlorinated to form vinyl chloride according to methods known in the art. In a chlorination reaction, chlorine or other chlorinating agent may be preferably co-fed to the reaction zone, and ethylene is chlorinated in the presence of a catalyst having activity for chlorinating ethylene to vinyl chloride (e.g. catalysts that include a metal halide or a metal oxyhalide, and preferably a halide or an oxyhalide of Cu, Fe, or Cr), or alternatively in the absence of a catalyst. In an oxychlorination reaction, a gaseous oxidant and HCl or other chlorinating agent may preferably be co-fed to the reaction zone, and ethylene is oxychlorinated in the presence of a catalyst having activity for oxychlorinating ethylene to vinyl chloride (e.g. catalysts that include a metal halide or a metal oxyhalide, preferably a halide or an oxyhalide of Cu, Fe, or Cr). Yet, ethylene may be oxidized to form ethylene oxide according to methods known in the art using a catalyst comprising an element or compound having activity for oxidizing ethylene to ethylene oxide (e.g. catalysts that include Ag, a halide thereof, an oxide thereof or a salt thereof). Ethylene glycol may be produced by oxidizing ethylene to faun ethylene oxide as described above, and hydrating ethylene oxide to form ethylene glycol. Ethylene carbonate may be produced from ethylene by reacting ethylene with carbon dioxide or carbon monoxide to form ethylene carbonate, or alternatively by forming ethylene glycol as described above and then reacting the ethylene glycol with phosgene. Ethyl acetate may be formed from acetic acid, prepared as described above, according to methods known in the art. Vinyl acetate may also be prepared by vapor-phase reaction of ethylene, acetic acid and oxygen over a Pd catalyst.

In one embodiment, the product stream includes propylene as a non-butene compound. In some embodiments, propylene produced via oxidative dehydrogenation of propane using the bimetallic catalyst may be further reacted to form polypropylene, acrolein, acrylic acid, acetone, propylene oxide, and propylene carbonate. Propylene may be optionally purified, and then further reacted according to one or more of the following schemes. For example, in one embodiment, propylene can be polymerized to foil polypropylene according to methods known in the art using a catalyst having activity for polymerizing propylene to polypropylene (e.g. aluminum alkyl catalysts). In another embodiment, propylene is oxidized to form acrolein according to methods known in the art using a catalyst comprising an element or compound having activity for oxidizing propylene to acrolein (e.g. catalysts that include an oxide of Bi, Mo, Te or W, or mixtures of such oxides). In another embodiment, propylene is oxidized to form acrylic acid according to methods known in the art using a catalyst comprising an element or compound having activity for oxidizing propylene to acrylic acid (e.g. catalysts that include an oxide of Mo, V or W, or mixtures of such oxides). Acetone may be produced from propylene by oxidation of propylene. Propylene may also be oxidized to form propylene oxide according to methods known in the art using a catalyst comprising an element or compound having activity for oxidizing propylene to propylene oxide (e.g. catalysts that include TiSi oxide or PdTiSi oxide). In one embodiment, propylene carbonate is formed by preparing propylene oxide as described above, and by reacting the propylene oxide with carbon dioxide. Propylene can also be directly converted to propylene carbonate in a single-step process.

In a preferred embodiment, the butane-containing hydrocarbon stream, the oxidant, the bimetallic catalyst loading, and reaction conditions are controlled to achieve a reaction performance that is suitable for industrial applications. Accordingly, in one embodiment, the butane-containing hydrocarbon stream, the oxidant, the bimetallic catalyst loading, and reaction conditions are controlled such that butane is dehydrogenated to butene (i.e. 1-butene, cis-2-butene, trans-2-butene, 1,3-butadiene, and isobutylene) with a butane conversion of at least about 5% by mole, preferably at least about 10% by mole, preferably at least about 15% by mole, preferably at least about 20% by mole, preferably at least about 25% by mole, but no more than 30% by mole, and a selectivity of at least about 70% by mole, preferably at least about 75% by mole, preferably at least about 80% by mole, preferably at least about 85% by mole, preferably at least about 90% by mole. In another embodiment, the butane-containing hydrocarbon stream, the oxidant, the bimetallic catalyst loading, and reaction conditions are controlled such that butane is dehydrogenated to butene (i.e. 1-butene, cis-2-butene, trans-2-butene, 1,3-butadiene, and isobutylene) with a butane conversion in the range of 5% to 30% by mole, preferably 8% to 25% by mole, preferably 10% to 22% by mole, preferably 11% to 20% by mole, preferably 15% to 20% by mole, and a selectivity of the butene compounds in the range of 80% to 95% by mole, preferably 82% to 92% by mole, preferably 85% to 90% by mole. In some embodiments, a selectivity of 1-butene is in the range of 3% to 20% by mole, preferably 5% to 18% by mole, preferably 10% to 15% by mole; a selectivity of 1,3-butadiene is in the range of 20% to 70% by mole, preferably 30% to 60% by mole, preferably 40% to 50% by mole; a selectivity of oxygenation and cracking reactions is in the range of 0.5% to 15% by mole, preferably 5% to 18% by mole, preferably 10% to 15% by mole; and a selectivity of partial oxidation reactions is in the range of 0.5% to 10% by mole, preferably 1% to 8% by mole, preferably 3% to 6% by mole.

As used herein, the term "butane conversion" refers to the percentage of the amount (by mole) of butane provided to a reaction zone of a reactor via the butane-containing hydrocarbon stream, which is converted to carbon products.

As used herein, the term "selectivity" refers to the percentage of the amount (by mole) of butane that is converted to the butene compound (i.e. 1-butene, cis-2-butene, trans-2-butene, 1,3-butadiene, and isobutylene). In addition, the selectivity of oxygenation and cracking reactions refers to the amount (by mole) of butane that is converted via oxygenation and cracking reactions, and the selectivity of partial oxidation reactions refers to the amount (by mole) of butane that is converted via partial oxidation reactions. Alternatively, the "selectivity" is defined as a molar atio of the butene compound to the non-butene compounds present in the product stream. In one embodiment, the selectivity is substantially independent of the butane conversion.

In view of the above definitions of the butane conversion and the selectivity, a yield of the butene compound based on the butane conversion may be defined as a multiplication of the butane conversion and the selectivity. Accordingly, in one embodiment, the yield of the butene compound is in the range of 5% to 20%, preferably 6% to 15%, preferably 7% to 10%, based on the butane conversion, which is in the range of 5% to 30%, preferably 8% to 25%, preferably 10% to 22%, preferably 11% to 20%, preferably 15% to 20%.

The bimetallic catalyst of the present invention offers significant performance advantages as compared to currently used catalysts for oxidative dehydrogenation of butane such as VMo, MgO/ZrO$_2$, or VMgO/MgO/ZrO$_2$ catalysts. For example, the catalysts of the invention may result a butane conversion of about 15% to 20% and a selectivity of about 85% to 90%, compared to a butane conversion of about 5% conversion and a selectivity of about 90% for currently used catalysts.

In one embodiment, the bimetallic catalyst of the present disclosure is stable with respect to a dehydrogenation activity and performance characteristics. Stability of the bimetallic catalyst can be demonstrated by a lifetime testing, wherein the butane-containing hydrocarbon stream and the oxidant are co-fed to a reaction zone of a reactor containing the bimetallic catalyst, while maintaining the reaction zone (and the bimetallic catalyst) at a temperature that ranges from about 200° C. to about 600° C., preferably from about 300° C. to about 550° C., preferably from about 350° C. to about 520° C., preferably from about 375° C. to about 500° C., preferably from about 390° C. to about 475° C., preferably from about 400° C. to about 470° C. The butane-containing hydrocarbon stream is contacted with the bimetallic catalyst in the presence of the oxidant to dehydrogenate butane (and other alkanes present in the butane-containing hydrocarbon stream) and to form butene and other corresponding alkenes. The butene and other produced alkenes, unreacted alkanes and unreacted oxidants are exhausted or otherwise removed from the reaction zone. In a preferred embodiment, the steps of contacting the butane-containing hydrocarbon stream and the oxidant with the catalyst, dehydrogenating the alkanes, and exhausting the alkenes and unreacted reactants are carried out in a cumulative period of not less than about 200 hours, preferably not less than about 400 hours, more preferably not less than about 600 hours, even more preferably not less than about 1000 hours, and most preferably not less than about 2000 hours. Accordingly, the bimetallic catalyst may preferably be stable for at least about 5000 hours, and more preferably at least about 8000 hours.

In one embodiment, the bimetallic catalyst is treated with an inert gas before contacting the butane-containing hydrocarbon stream and the oxidant with the catalyst. The inert gas is preferably at least one selected from nitrogen, argon, helium and carbon dioxide. Treating the bimetallic catalyst is performed to bring a temperature of the catalyst to a preferable temperature, in which oxidative dehydrogenation is carried out. In view of that, the inert gas may have a temperature from about 200° C. to about 600° C., preferably from about 300° C. to about 550° C., preferably from about 350° C. to about 520° C., preferably from about 375° C. to about 500° C., preferably from about 390° C. to about 475° C., preferably from about 400° C. to about 470° C.

In another embodiment, at least a portion of the product stream is recycled to be contacted with the bimetallic catalyst. Recycling at least a portion of the product stream may result in an overall improvement in the butane conversion and the selectivity. For example, in one embodiment, recycling at least a portion of the product stream may increase the butane conversion by at least 5%, preferably at least 10%, but no more than 30%. In a preferred embodiment, unreacted alkanes of the product stream are first separated from the butene compounds, and then the unreacted alkanes are recycled to be contacted with the bimetallic catalyst.

Although the present disclosure is described and exemplified primarily in connection with oxidative dehydrogenation of butane, dehydrogenation of other alkanes using the bimetallic catalyst and the method disclosed herein may also be contemplated, and is within the scope of the invention. For example, cyclohexane may be oxidatively dehydrogenated over the bimetallic catalyst of the invention to form benzene. Moreover, the bimetallic catalyst of the invention may be used for dehydrogenating alkenes to one or more dehydrogenation products, e.g. dienes or alkynes. Accordingly, butene may be dehydrogenated to form butadiene, and isoamylene may be dehydrogenated to form isoprene.

According to a third aspect, the present disclosure relates to a method of producing the bimetallic catalyst. The method involves dissolving a nickel precursor and a bismuth precursor in water, preferably deionized water, to form a Ni—Bi solution. In a preferred embodiment, the nickel precursor is a metal salt of nickel and a counterion selected from nitrate, acetate, oxalate, and a halide. For example, in one embodiment, the nickel precursor is nickel nitrate, preferably nickel nitrate hexahydrate. In another preferred embodiment, the bismuth precursor is a metal salt of bismuth and a counterion selected from nitrate, acetate, oxalate, and a halide. For example, in one embodiment, the bismuth precursor is bismuth nitrate, preferably bismuth nitrate pentahydrate.

The nickel and the bismuth precursors may be in the form of a sol-gel that include nickel or bismuth along with one or more counterions selected from nitrate, acetate, oxalate, a halide, and an alkoxide. Additionally, the nickel and the bismuth precursors may be dissolved in an organic solvent (e.g. methanol, toluene, tetrahydrofuran, etc.). When a halide is used as a counterion, a resulting bimetallic catalyst is preferably rinsed with water to remove halide. For example, in one embodiment, the nickel precursor is nickel nitrate along with potassium bromide, wherein a resulting bimetallic catalyst is preferably rinsed with water to remove potassium bromide.

In one embodiment, the Ni—Bi solution further includes a third precursor to provide the third element to the bimetallic catalyst. The third precursor may preferably be a salt of Ti, Nb, Ta, and Zr, for example, titanium oxalate, niobium oxalate, tantalum oxalate, or zirconium oxalate.

In one embodiment, a concentration of nickel in the Ni—Bi solution is in the range of 5 to 7 g/L, preferably 5.2 to 6.8 g/L, preferably 5.5 to 6.7 g/L, preferably 5.8 to 6.5 g/L, preferably about 6.2 g/L. In another embodiment, a concentration of bismuth in the Ni—Bi solution is in the range of 7 to 9 g/L, preferably 7.5 to 8.9 g/L, preferably 8 to 8.8 g/L, preferably 8.5 to 8.7 g/L, preferably about 8.65 g/L. To achieve the Ni—Bi solution having the aforementioned concentration of nickel and bismuth, in one embodiment, 0.75 to 1.25 g, preferably 0.95 to 1.05 g, preferably about 1 g of the nickel precursor is dissolved in 140 to 180 ml, preferably 150 to 170 ml, preferably 160 ml of water, preferably distilled water. Then, 1.3 to 1.5 g, preferably 1.35 to 1.45 g, preferably about 1.39 g of the bismuth precursor is mixed with the resulting solution to form the Ni—Bi solution. Preferably, the Ni—Bi solution may be stirred at an elevated temperature of 30 to 70° C., preferably 40 to 65° C., preferably 50 to 60° C., preferably about 55° C. to dissolve the nickel and the bismuth precursor in water. In the embodiments where a third precursor is present to provide the third element to the composition of the bimetallic catalyst, a concentration of the third element in the Ni—Bi solution is no more than 2 g/L, preferably no more than 1 g/L, preferably no more than 0.5 g/L.

The method further involves mixing and stirring titanium carbide particles with the Ni—Bi solution to form a suspension. The suspension is maintained at a temperature in the range of 20 to 60° C., preferably 24 to 50° C., preferably 26 to 40° C., preferably about 25° C., for at least 6 hours, preferably at least 8 hours, preferably at least 12 hours, preferably at least 24 hours, during which nickel and bismuth are deposited on a surface of the titanium carbide particles and/or impregnated into the titanium carbide particles. In a preferred embodiment, a weight ratio of bismuth to nickel in the suspension is in the range of 1:1 to 2:1, preferably in the range of 1.2:1 to 1.5:1, preferably about 1.4:1. In a preferred embodiment, a ratio of the amount of the titanium carbide particles to a volume of the Ni—Bi solution depends on a pore volume of the titanium carbide particles, and may range from about 50 to about 150, preferably from about 70 to about 90 times the pore volume of the titanium carbide particles. For example, in one embodiment, 1.5 to 2.5 g, preferably 2 g of titanium carbide particles are used for 140 to 180 ml, preferably 150 to 170 ml, preferably 160 ml of the Ni—Bi solution, wherein the titanium carbide particles have a specific pore volume in the range of 0.5 to 3 ml/g, preferably about 1.5 ml/g. In one embodiment, a pH of the suspension is maintained at about 2 to about 6.5, preferably about 3 to about 6, preferably about 4 to about 6.

The method further involves drying the suspension. Accordingly, the suspension may be dried preferably at a reduced pressure (i.e. a sub atmospheric pressure of less than 0.9 atm, preferably less than 0.5 atm), and at a temperature ranging from about 80° C. to about 150° C., preferably from about 100° C. to about 140° C., preferably about 120° C., for a period of time ranging from about 1 hour to about 5 hours, preferably 2 to 4 hours, preferably about 3 hours.

Alternatively, the suspension may be dried by other methods known in the art such as lyophilization, precipitation, and/or evaporation. Lyophilization refers to freezing the suspension (e.g., under liquid nitrogen), and then placing a frozen suspension in a vacuum so that water (i.e. ice) sublimes, leaving behind a solid pre-calcination composition that includes the bimetallic catalyst. Precipitation refers to a method of separating a solute from a solvent via adding one or more chemical reagents that can selectively precipitate the solute (i.e. the bimetallic catalyst) from the solvent (i.e. water). The chemical reagents may provide ions that shift ionic equilibrium to favor formation of insoluble metal salts, or may bind with bismuth, nickel, or other elements present on the titanium carbide catalyst support to form uncharged and water insoluble coordination compounds. The chemical reagents may also oxidize or reduce bismuth, nickel, or other elements present on the titanium carbide catalyst support to form ionic species that produce water insoluble salts. Regardless of a precipitation mechanism used, precipitated compounds (i.e. the bimetallic catalyst) may be separated from the remaining suspension by first centrifuging the suspension and then decanting a supernatant. Residual water present in the solid pre-calcination composition may be removed by evaporation via heating and/or under vacuum. Preferably, the solid pre-calcination composition may be achieved in a form of a powder that includes the bimetallic catalyst.

In some embodiments, the method further involves pressing the powder to form pellets of the bimetallic catalyst with an average pellet particle size in the range of 0.1 to 2 mm, preferably 0.2-1.5 mm, more preferably 0.4 to 1 mm, even more preferably 0.5 to 0.9 mm. The pellets may further be crushed to form bimetallic catalyst granules, and said granules may further be sieved to form finer granules with an average particle size in the range of 0.1 to 1 mm, preferably 0.2-0.8 mm. Having the bimetallic catalyst in the form of pellets or granules may provide a consistent bulk density of the catalyst and/or a consistent pressure drop across a catalyst bed of a reactor that houses the bimetallic catalyst.

In a preferred embodiment, the bimetallic catalyst granules is calcined via a two-step calcining process, wherein the bimetallic catalyst granules is first calcined at a temperature in the range of 300 to 400° C., preferably 320 to 380° C., preferably 340 to 360° C., preferably about 350° C., for no more than 2 hours, preferably no more than 1 hour. Next, the already calcined catalyst is calcined for a second time at a temperature in the range of 500 to 700° C., preferably 550 to 650° C., preferably 570 to 620° C., preferably about 590° C., for no more than 3 hours, preferably no more than 2 hours. Preferably, the two-step calcining process is carried out in an inert atmosphere, for example, under a constant flow of an inert gas (e.g. argon, helium, nitrogen, etc.).

The examples below are intended to further illustrate protocols for the method of dehydrogenating the butane-containing hydrocarbon stream and the method of producing the bimetallic catalyst, and are not intended to limit the scope of the claims.

Example 1—Catalyst Preparation

Bi—Ni oxide based catalysts reported in this invention were prepared using co-impregnation technique, using Ni(NO$_3$)$_2$·6H$_2$O (99% Fisher-Scientific) and Bi(NO$_3$)$_3$·5H$_2$O (98%), Fluka-Garantie) as precursors for the metals. For synthesizing 30 wt % Bi-20 wt % Ni/TiC catalyst, 0.99 g of nickel nitrate hexahydrate was dissolved in 160 ml of distilled rater, then 1.392 g of bismuth nitrate pentahydrate was successfully added to the mixture while stirring at 55° C. 2 g of TiC support was added and thoroughly stirred for dissolution. Then, the resultant suspension was left overnight for impregnation. After drying the suspension for 3 h at 120° C., the resulting powder was pressed into pellets form, crushed to break up the crumbs and then sieved into 500-850 mesh granules.

For catalytic evaluation and characterization, the as-prepared catalyst was calcined using two step calcination method, where the catalyst is heated to a temperature of 350° C. at rate of 10° C. per minute and held for 1 hour after which it was raised again at rate of 15° C. per minute to temperature of 590° C. and kept for 2 hours under flowing nitrogen.

Example 2

The performance of the as-prepared catalysts was examined using a fixed bed type of reactor with continuous flow system (BELCAT). It comprises a quartz tubular reactor, placed inside stainless steel furnace which passes through the reactor furnace thermo well wall. Typically 300 mg of the as-synthesized catalyst (500-850 microns) was placed into the quartz reaction tube (length of heating zone=18 cm, inner diameter=8 mm) Prior to the reaction, the as-synthesized sample of the catalyst was pretreated at high temperature under flowing nitrogen. After which the catalyst was cooled down to the reaction temperature using nitrogen. Then, catalytic tests were performed at reaction temperature of (400, 450 and 500° C.) and different reactant feed ratio (O$_2$:n-C$_4$H$_{10}$=1.0, 2.0, and 4.0 mol·mol$^{-1}$).

Taking into account the exothermic nature of oxy-dehydrogenation reaction, the catalyst bed temperature was monitored with the help of thermocouple, which inserted into thermocouple well. The products and reactants were analyzed with the help of an Agilent 7890N gas chromatograph. The GC is equipped with HD (N$_2$ carrier) and GC-GasPro capillary column (length=600 cm, internal diameter=0.032 cm) for analyzing the hydrocarbons and oxygenates. The thermal conductivity detector (TCD), Shin Carbon 80/100 mesh SS Column (Helium as a carrier gas) and MS5A 60/80 mesh SS Column (Argon as a carrier gas) were also attached with the GC system for detection of gases including CO, CO$_2$, O$_2$, N$_2$ and H$_2$. The effluents were identified by comparing with authentic samples. The conversion of n-butane and selectivity of products were determined on the basis of carbon balance.

Example 3

The reaction temperature and oxygen to n-butane ratio play a key role in the catalyst performance. Therefore, the reaction pathways were investigated for the catalyst by changing these two parameters. The effluent stream consists mainly of dehydrogenated products (1-C$_4$H$_8$, cis-2-C$_4$H$_8$, trans-2-C$_4$H$_8$, and and 1,3-butadiene), cracked products (C$_2$H$_4$ and C$_3$H$_6$), and partial oxidation (Carbon monoxide), while light paraffins (C1, C2 and C3), CO$_2$ and oxygenates were also detected at negligible amounts. The catalyst performance for oxy-dehydrogenation of n-butane to high value unsaturated C$_4$ products (1,3-butadiene and butenes) at different reaction conditions (Temperature and feed ratio of O$_2$:n-C$_4$H$_{10}$) is shown in Table 1.

Table 1 shows the maximum selectivity of 93.8% towards dehydrogenated products at 400° C., while the maximum yield for 1,3-butadiene (BD) occurred at 450° C. with a BD selectivity of 50.7% and a conversion of about 17%. The partial oxidation product was found to be negligible even at high temperature, while the cracking products (ethylene and propylene) were increased at higher temperature (500° C.). These results show that the as-synthesized catalyst is highly selective for dehydrogenated products (C$_4$ olefins and 1,3-butadiene) and outperformed what s reported in prior art.

TABLE 1

Catalytic performances for 30 wt. % Bi-20 wt. % Ni oxide/Titanium Carbide catalyst at reaction temperatures of 400, 450 and 500° C., and different molar feed ratio (O$_2$: n-butane = 1.0, 2.0 and 4.0).

| Temp (° C.)-O$_2$/n-C$_4$H$_{10}$ | 400-1 | 400-2 | 400-4 | 450-2 | 500-2 |
|---|---|---|---|---|---|
| n-C$_4$H$_{10}$ conversion [%] | 8.1 | 11.5 | 17.4 | 16.6 | 29.2 |
| Selectivity [C %] | | | | | |
| DH | 93.8 | 89.0 | 82.5 | 83.7 | 35.3 |
| 1-C$_4$H$_8$ | 13.6 | 12.1 | 14.7 | 13.6 | 5.8 |
| BD | 47.5 | 51.1 | 46.3 | 50.7 | 22.4 |
| ° C. | 1.7 | 5.7 | 11.1 | 12.3 | 63.3 |
| PO | 4.5 | 5.3 | 6.4 | 4.0 | 1.4 |
| BD/DH | 50.7 | 57.4 | 56.2 | 60.6 | 63.4 |
| (1-C$_4$= + BD)/DH | 65.2 | 71.1 | 74.0 | 76.9 | 79.6 |
| BD/(1-C$_4$= + BD) | 77.7 | 80.8 | 75.9 | 78.9 | 79.6 |
| BD yield | 3.8 | 5.9 | 8.1 | 8.4 | 6.5 |
| DH yield | 7.6 | 10.2 | 14.3 | 13.9 | 10.3 |

DH stands for "dehydrogenation & isomerization", BD: 1,3-butadiene, ° C.: oxygenates & cracking PO: partial oxidation.

The invention claimed is:

1. A method of dehydrogenating a butane-containing hydrocarbon stream, comprising:
contacting the butane-containing hydrocarbon stream with a bimetallic catalyst in the presence of oxygen to form a product stream comprising a butene compound, wherein the bimetallic catalyst consists of nickel oxide and bismuth oxide on a titanium carbide catalyst support.

2. The method of claim 1, wherein the butene compound is one or more of 1-butene, cis-2-butene, trans-2-butene, 1,3-butadiene, and isobutylene.

3. The method of claim 1, wherein a weight percent of nickel in the bimetallic catalyst is within a range of 15 wt % to 25 wt %, relative to the total weight of the bimetallic catalyst.

4. The method of claim 1, wherein a weight percent of bismuth in the bimetallic catalyst is within a range of 25 wt % to 35 wt %, relative to the total weight of the bimetallic catalyst.

5. The method of claim 1, wherein the butane-containing hydrocarbon stream is contacted with the bimetallic catalyst at a temperature of 400 to 450° C.

6. The method of claim 1, wherein a volume fraction of butane in the butane-containing hydrocarbon stream is at least 0.9.

7. The method of claim 1, wherein a molar ratio of oxygen to butane is in a range of 1:1 to 4:1.

8. The method of claim 1, wherein the bimetallic catalyst has an average particle size in a range of 0.1 to 2 mm.

9. The method of claim 1, wherein the product stream further comprises non-butene compounds, and wherein a molar ratio of the butene compound to the non-butene compounds is at least 0.8.

10. The method of claim 1, wherein a conversion of butane is in a range of 5 to 30 mol %, and wherein a yield of the butene compound is in a range of 5% to 20% based on the conversion of butane.

11. The method of claim 1, further comprising:
treating the bimetallic catalyst with an inert gas having a temperature in a range of 300 to 500° C. prior to the contacting.

12. The method of claim 1, further comprising:
mixing the butane-containing hydrocarbon stream with an inert gas to form a gaseous mixture prior to the contacting, wherein a volume fraction of the butane-containing hydrocarbon stream in the gaseous mixture is within a range of 0.01 to 0.1.

13. The method of claim 1, wherein the butane-containing hydrocarbon stream is contacted with the bimetallic catalyst at a temperature of 400 to 450° C., and wherein a molar ratio of oxygen to butane is in a range of 1:1 to 4:1.

14. A method of dehydrogenating a butane-containing hydrocarbon stream, comprising:
contacting the butane-containing hydrocarbon stream with a bimetallic catalyst in the presence of oxygen to form a product stream comprising a butene compound,
wherein the bimetallic catalyst comprises nickel and bismuth on a titanium carbide catalyst support, and
wherein the butane-containing hydrocarbon stream is contacted with the bimetallic catalyst at a temperature of 400 to 450° C.

15. The method of claim 14, wherein a molar ratio of oxygen to butane is in a range of 1:1 to 4:1.

* * * * *

UNITED STATES PATENT AND TRADEMARK OFFICE
CERTIFICATE OF CORRECTION

PATENT NO. : 10,125,061 B2
APPLICATION NO. : 15/487155
DATED : November 13, 2018
INVENTOR(S) : Isam Aljundi It is certified that error appears in the above-identified patent and that said Letters Patent is hereby corrected as shown below:

On the Title Page

Item (72):
Please change "(72) Inventor: Isam Aljundi, Dhahran, Saudi Arabia" to
-- (72) Inventors: Sulaiman S. Alkhattaf, Dhahran, Saudi Arabia
    Isam Aljundi, Dhahran, Saudi Arabia
    Omer Elmutasim Elmahadi, Dhahran, Saudi Arabia --.

Signed and Sealed this
Ninth Day of July, 2019

Andrei Iancu
*Director of the United States Patent and Trademark Office*